(12) United States Patent
Apostolo et al.

(10) Patent No.: US 8,940,944 B2
(45) Date of Patent: *Jan. 27, 2015

(54) FLUOROELASTOMERS

(75) Inventors: Marco Apostolo, Novara (IT); Francesco Triulzi, Milan (IT); Vito Tortelli, Milan (IT); Marco Galimberti, Bollate Milano (IT)

(73) Assignee: Solvay Solexis S.p.A., Milan (IT)

( * ) Notice: Subject to any disclaimer, the term of this patent is extended or adjusted under 35 U.S.C. 154(b) by 274 days.

This patent is subject to a terminal disclaimer.

(21) Appl. No.: 13/427,656

(22) Filed: Mar. 22, 2012

(65) Prior Publication Data

US 2012/0226077 A1 Sep. 6, 2012

Related U.S. Application Data

(60) Continuation of application No. 12/394,811, filed on Feb. 27, 2009, now abandoned, which is a division of application No. 11/190,893, filed on Jul. 28, 2005, now Pat. No. 7,514,512.

(30) Foreign Application Priority Data

Jul. 30, 2004 (IT) .............................. MI2004A1573

(51) Int. Cl.
*C07C 41/54* (2006.01)
*C08F 14/18* (2006.01)

(52) U.S. Cl.
USPC .......................................... 568/596; 526/247

(58) Field of Classification Search
USPC .......................................... 568/596; 526/247
See application file for complete search history.

(56) References Cited

U.S. PATENT DOCUMENTS

| | | |
|---|---|---|
| 3,085,083 A | 4/1963 | Schreyer |
| 3,132,123 A | 5/1964 | Harris et al. |
| 3,450,684 A | 6/1969 | Darby |
| 3,635,926 A | 1/1972 | Gresham et al. |
| 3,752,787 A | 8/1973 | de Brunner |
| 3,810,874 A | 5/1974 | Mitsch et al. |
| 3,817,960 A | 6/1974 | Resnick |
| 3,876,654 A | 4/1975 | Pattison |
| 3,896,179 A | 7/1975 | Resnick |
| 4,035,565 A | 7/1977 | Apotheker et al. |
| 4,214,060 A | 7/1980 | Apotheker et al. |
| 4,233,427 A | 11/1980 | Bargain et al. |
| 4,243,770 A | 1/1981 | Tatemoto et al. |
| 4,259,463 A | 3/1981 | Moggi et al. |
| 4,358,412 A | 11/1982 | Ezzell et al. |
| 4,400,872 A | 8/1983 | Berges |
| 4,487,903 A | 12/1984 | Tatemoto et al. |
| 4,501,869 A | 2/1985 | Tatemoto et al. |
| 4,564,662 A | 1/1986 | Albin |
| 4,694,045 A | 9/1987 | Moore |
| 4,745,165 A | 5/1988 | Arcella et al. |
| 4,766,190 A | 8/1988 | Morita et al. |
| 4,789,717 A | 12/1988 | Giannetti et al. |
| 4,831,085 A | 5/1989 | Okabe et al. |
| 4,864,006 A | 9/1989 | Giannetti et al. |
| 4,906,770 A * | 3/1990 | Marchionni et al. .......... 560/300 |
| 4,943,622 A | 7/1990 | Naraki et al. |
| 4,990,283 A | 2/1991 | Visca et al. |
| 5,260,393 A | 11/1993 | Arcella et al. |
| 5,401,818 A | 3/1995 | Oka et al. |
| 5,696,216 A | 12/1997 | Kruger et al. |
| 5,777,179 A | 7/1998 | Liang et al. |
| 6,255,536 B1 | 7/2001 | Worm et al. |
| 6,310,142 B1 | 10/2001 | Apostolo et al. |
| 6,395,834 B1 | 5/2002 | Albano et al. |
| 6,730,760 B2 | 5/2004 | Grootaert et al. |
| 7,019,177 B2 * | 3/2006 | Tortelli et al. ................. 568/615 |
| 7,148,300 B2 | 12/2006 | Fukushi et al. |
| 7,544,752 B2 * | 6/2009 | Triulzi et al. ................. 526/247 |
| 2004/0186324 A1* | 9/2004 | Tortelli et al. ................. 568/661 |

FOREIGN PATENT DOCUMENTS

| | | |
|---|---|---|
| EP | 0 120 462 A1 | 10/1984 |
| EP | 0 130 052 A1 | 1/1985 |
| EP | 0 136 596 A2 | 4/1985 |
| EP | 0 178 935 A1 | 4/1986 |
| EP | 0 182 299 A2 | 5/1986 |
| EP | 0 199 138 B1 | 2/1989 |
| EP | 0 355 705 A1 | 10/1989 |
| EP | 0 407 937 A1 | 1/1991 |
| EP | 0 410 351 A1 | 1/1991 |
| EP | 0 647 609 A | 4/1995 |
| EP | 0 661 304 B1 | 5/1995 |
| EP | 0 683 149 B1 | 11/1995 |
| EP | 0 684 277 A1 | 11/1995 |
| EP | 1 117 710 B1 | 7/2001 |
| EP | 1 148 041 A2 | 10/2001 |
| EP | 1148072 A2 * | 10/2001 |
| EP | 1172380 A2 * | 1/2002 |
| EP | 1260550 A1 * | 11/2002 |
| EP | 1 304 341 A2 | 4/2003 |
| EP | 1 304 341 A3 | 4/2003 |
| EP | 1 308 457 A2 | 5/2003 |
| EP | 1308467 A2 * | 5/2003 |
| EP | 1621559 A2 * | 2/2006 |
| JP | 2004163927 | 10/2004 |
| WO | 99/48939 | 9/1999 |
| WO | WO 00/12574 A1 | 3/2000 |

OTHER PUBLICATIONS

Maskornik et al., "ECD-006 Perfluoroelastomer A High Performance Engineering Material", Soc. Plast Eng. Tech. Pao. 20 675-677, 1974.
J. Macromol. Sci-Phys. B1(4), 815-830, 1967.
Pianca et al., "End Group in Fluoropolymers", J. Fluorine Chem, 95. 71-84. 1999.
Knunyants et al., Izv. Akad Nauk. SSSR. Ser. Khim, 2. 384-386, 1964 (corresponding to pp. 358-361 of English translation.

* cited by examiner

*Primary Examiner* — Peter D. Mulcahy
*Assistant Examiner* — Henry Hu
(74) *Attorney, Agent, or Firm* — Arent Fox LLP

(57) ABSTRACT

VDF-based curable fluoroelastomers having glass transition temperature lower than −35° C. and an amount of —COF end groups in the polymer lower than the sensitivity limit of the method using the FT-IR spectroscopy described in the present application.

17 Claims, No Drawings

FLUOROELASTOMERS

CROSS REFERENCE TO RELATED APPLICATIONS

This application is a continuation of U.S. patent application Ser. No. 12/394,811 filed Feb. 27, 2009, now abandoned, which is a divisional of U.S. patent application Ser. No. 11/190,893 filed Jul. 28, 2005, now U.S. Pat. No. 7,514,512 issued Apr. 7, 2009, which claims priority from Italian patent Application No. MI2004 A 001573 filed Jul. 30, 2004. The entire contents of this application is incorporated herein by reference.

The present invention relates to VDF-based fluoroelastomers having a Tg (glass transition temperature) lower than −35° C. and an improved combination of mechanical and compression set properties in a wide range of temperatures, at high and at low temperatures.

More specifically the present invention relates to fluoroelastomers having a Tg lower than −35° C. and substantially —COF end group free, said end groups being undetectable with the method indicated hereinafter. The fluoroelastomers of the present invention show an improved molecular weight as shown by the improved intrinsic viscosity and are obtainable by a polymerization process with an improved productivity.

It is well known that fluoroelastomers are polymers particularly useful in the fields of the automotive, aerospace, oil, petrochemical and electronic industry due to their combination of thermal and chemical resistance and of maintenance of good mechanical and compression set properties. However it is necessary that these polymers have an improved combination of the above properties in a wide temperature range, at high and at low temperatures.

Various fluoroelastomers have been suggested in the prior art to obtain the combination of the above properties, highly requested by fluoroelastomer users. However the —COF end group values in fluoroelastomers are not reported in the prior art. The Applicant, after deep researches, has found that, if the polymerization brings to polymers having —COF end groups, the fluoroelastomers obtainable therefrom do not show high mechanical and elastic properties.

Various fluoroelastomers wherein the glass transition temperature (Tg) values are reported are known in the prior art. However in the prior art the combination of a low Tg and of improved mechanical and elastomeric properties at high and at low temperatures is not obtained.

U.S. Pat. No. 3,132,123 describes the preparation of perfluoroalkylvinylethers, their homopolymers and copolymers with TFE. The homopolymers are obtained under extreme experimental conditions, by using polymerization pressures from 4,000 to 18,000 atm. The general formula of the described vinylethers is the following:

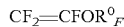

wherein $R^0_F$ is a perfluoroalkyl radical preferably from 1 to 5 carbon atoms. Tests carried out by the Applicant have shown that the homopolymer Tg is not very low and is of the order of −6° C.

U.S. Pat. No. 3,450,684 relates to vinylethers of formula:

wherein $X^0$=F, Cl, $CF_3$, H and n' can range from 1 to 20. Also the homopolymers obtained by UV polymerization are reported. The exemplified copolymers are not characterized with their mechanical and elastomeric properties at low temperatures.

U.S. Pat. No. 3,635,926 relates to the emulsion copolymerization of perfluorovinylethers with TFE. It is stressed that the presence of —COF end groups makes the polymers unstable. The same was already reported in U.S. Pat. No. 3,085,083 in the polymerization systems of perfluorovinylethers in solvent.

U.S. Pat. No. 3,817,960 relates to the preparation and polymerization of perfluorovinylethers of formula:

wherein n" can range from 1 to 5. The vinylether synthesis is complex. No characterization data on the above mentioned properties are reported.

U.S. Pat. No. 3,896,179 relates to the separation of "primary" perfluorovinylether isomers, for example of $CF_3CF_2CF_2OCF=CF_2$ from the respective "secondary" less stable isomers $CF_3(CF_3)CFOCF=CF_2$. The latter are undesired products as regards the polymer preparation and the poor properties of the obtained polymers.

U.S. Pat. No. 4,487,903 refers to the preparation fluoroelastomeric copolymers using perfluoro vinylethers of formula:

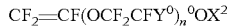

wherein $n^0$ ranges from 1 to 4; $Y^0$=F, Cl, $CF_3$, H; $X^2$ can be $C_1$-$C_3$ perfluoroalkyl, $C_1$-$C_3$ ω-hydroperfluoroalkyl, $C_1$-$C_3$ ω-chloroperfluoroalkyl. The polymer has a fluorovinylether unit content ranging from 15 to 50% by moles. Said vinylethers give copolymers having at low temperatures properties higher than those of the above mentioned perfluorovinylethers PVE (perfluoropropylvinyl-ether) and MVE type. In this patent it is disclosed, for having good properties at low temperature it is required the presence of at least two ether bonds in the side chain adjacent to the double bond. Furthermore from the patent for $n^0$ values higher than 4 it is difficult to purify the monomers and the effect on the polymer $T_g$ decrease is lower. Besides the reactivity of the described vinylethers is very low and it is difficult to obtain polymers having a high molecular weight capable to give good elastomeric properties for the mentioned applications. A TFE/perfluorovinylether copolymer ($n^0$=2) 31/69% by weight with Tg of −32° C. is exemplified. However the polymer is obtained with very long reaction times (96 hours of polymerization). Also in this case no characterization data of the cured elastomer are given.

EP 130,052 describes the polymerization of perfluorovinylpolyethers (PVPE) which leads to amorphous perfluoropolymers having a $T_g$ ranging from −15° to −100° C. In the patent copolymers and terpolymers of TFE and MVE with vinylethers (PVPE) of formula:

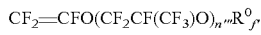

are described, wherein n'" ranges from 3 to 30 and $R^0_f$ is a perfluoroalkyl. Owing to purification difficulties, the used vinylethers are vinylether mixtures with different n'" values. According to this patent the most marked effect on the $T_g$ decrease is shown when n'" is equal to or higher than 3, preferably higher than 4. According to the polymerization examples described in said patent, the final polymer mass, besides the hot and under vacuum treatment, must then be washed with Freon® TF to remove all the unreacted monomer (PVPE). From the Examples it can be seen that the reactivity of all the described monomers (PVPE) is poor.

U.S. Pat. No. 4,766,190 relates to the polymerization of perfluorovinylpolyethers (PVPE) similar to those of U.S. Pat. No. 4,487,903 with TFE and low perfluoropropene percentages, to increase the mechanical properties of the obtained polymers.

U.S. Pat. No. 5,401,818 relates to the preparation of perfluorovinylethers of formula:

$$R^1{}_f(OCF_2CF_2CF_2)_{m'}—OCF=CF_2$$

(wherein $R^1{}_f$ is a $C_1$-$C_3$ perfluoroalkyl radical and m' an integer ranging from 1 to 4) and of the respective copolymers having improved properties at low temperature. The preparation of said perfluorovinylethers takes place by 7 steps, of which some have very low yields, and comprising also a perfluorination with elemental $F_2$. The reactivity of said perfluorovinylethers is anyway low.

Other problems shown by the prior art relate to the low perfluorovinylether reactivity, making necessary the recovery from the reaction raw products of the unreacted monomers (British patent GB 1,514,700), and the stability problems for the polymers having —C(O)F end groups (U.S. Pat. No. 3,635,926). The latter can be further transformed with suitable reactants to increase the polymer stability (EP 178,935):

The perfluorooxyalkylvinylethers are furthermore used to give to fluorinated rubbers good properties at low temperatures and in particular to lower the glass transition temperature (Tg).

By increasing the perfluorooxyalkylene units, the Tg of the amorphous copolymers decreases, but at the same time the vinylether reactivity drastically decreases, making difficult or impossible to obtain polymers having a sufficiently high molecular weight to obtain polymers with good properties. Further the problems previously shown for the recovery of the unreacted monomer from the polymerization raw products or from the polymer itself are still present (U.S. Pat. No. 4,487, 903 EP 130,052).

The amorphous TFE copolymers with perfluoromethylvinylether have a $T_g$ of about 0° C. or slightly lower (Maskornik, M. et al. "ECD-006 Fluoroelastomer—A high performance engineering material", Soc. Plast Eng. Tech. Pao. (1974), 20, 675-7).

The PVDF homopolymer has a T value of about −47° C.

The extrapolated value of the $T_g$ for the MVE homopolymer is about −5° C. (J. Macromol. Sci.—Phys., B1(4), 815-830, December 1967).

Other patents describing vinylethers for obtaining fluoroelastomers are known. See U.S. Pat. Nos. 6,255,536, EP 1,117,710, WO 99/48,939 and 5,696,216.

More specifically fluoroelastomeric copolymers are known, suitable for preparing O-rings, based on monomeric units deriving from vinylidenfluoride (VDF), hexafluoropropene (HFP), perfluoroalkylvinylethers (PAVE) as for example methylvinylether, and optionally tetrafluoroethylene (TFE), which are ionically curable, have high elastomeric properties at low and high temperatures and show good processability, as mould release after curing (see U.S. Pat. No. 5,260,393). Said fluoroelastomers, however, have a glass transition temperature (Tg) higher than −35° C. They are not usable therefore at temperatures lower than −35° C. since they loss their elastomeric properties.

Patent application EP 1,308,467 describes perfluoroelastomers containing fluoroalkoxyvinylethers of formula $CFX_A\!=\!CX_AOCF_2OR_A$, wherein $X_A\!=\!F$, H; $R_A$ is $C_2$-$C_6$ perfluoroalkyl, perfluorooxyalkyl, or $C_5$-$C_6$ cyclic (per)fluoroalkyl. In particular the following perfluoroalkoxyvinylethers are described: $CF_2\!=\!CFOCF_2OCF_2CF_3$ (MOVE 1) and $CF_2\!=\!CFOCF_2OCF_2CF_2OCF_3$ (MOVE 2). In the Examples perfluoroelastomers containing at most about 40% of said perfluoroalkoxyvinylethers are described. The MOVE perfluoroelastomers with TFE contain —COF end groups. See the comparative Examples. To prepare polymeric compositions containing a TFE amount lower than or equal to 60% by moles it is necessary to use long polymerization times. From the industrial point of view this represents a drawback since the productivity is worsened.

EP 1.304.341 describes fluoroelastomers containing fluoroalkoxyvinylethers of formula $CFX_A\!=\!CX_AOCF_2OR_A$, wherein $X_A\!=\!F$, H; $R_A$ is $C_2$-$C_6$ perfluoroalkyl, perfluorooxyalkyl or $C_5$-$C_6$ cyclic (per)fluoroalkyl. In particular the following perfluoroalkoxyvinylethers are described: $CF_2\!=\!CFOCF_2OCF_2CF_3$ (MOVE 1) and $CF_2\!=\!CFOCF_2OCF_2CF_2OCF_3$ (MOVE 2). Fluoroelastomers containing at most mo more than 19% of said perfluoroalkoxyvinylethers are described in the Examples. Tests carried out by the Applicant have shown that said fluoroelastomers have —COF type end groups which, as said, worsen the mechanical properties at high temperatures and the thermal resistance of said polymers.

The need was felt to have available VDF-based fluoroelastomers having the following combination of properties:
Tg lower than −35° C., more preferably lower than −40° C., still more preferably lower than −45° C.;
substantially —COF end group free, said end groups being undetectable by the method indicated afterwards;
improved molecular weight, as shown from the higher value of the intrinsic viscosity;
improved mechanical and compression set properties in a wide temperature range, at high and at low temperatures;
improved productivity of the process for obtaining fluoroelastomers, expressed as (polymer Kg)/(hour×litre of water).

The Applicant has unexpectedly and surprisingly found fluoroelastomers having a surprisingly improved combination of the above properties.

It is an object of the present invention curable VDF-based fluoroelastomers having a glass transition temperature lower than −35° C., more preferably lower than −40° C., still more preferably lower than −45° C., and having an amount of —COF end groups lower than the sensitivity limit of the method described herein: at the end of the polymerization, the polymer is isolated by coagulation by freezing and subsequent defrosting; it is washed twice with demineralized water and is dried in a stove until a constant weight; the —COF end groups are determined by FT-IR spectroscopy, wherein on a polymer film having a thickness from 50 to 300 micron a scanning between 4000 cm$^{-1}$ and 400 cm$^{-1}$ is carried out, the film being then kept for 12 hours in an environment saturated with ammonia vapours and lastly recording the IR spectrum under the same conditions of the initial IR spectrum; elaborating the two spectra by subtracting to the signals of the spectrum of the untreated specimen (initial spectrum) the corresponding signals of the specimen spectrum after exposure to ammonia vapours, drawing the "difference" spectrum, normalized by the following equation:

$$\frac{\text{"Difference spectrum"}}{[\text{film weight (g)/film area (cm}^2)]};$$

the optical densities related to the —COF end groups, reacted with the ammonia vapours, are measured; the optical densities are converted into mmoles/kg of polymer by using the extinction coefficients reported in Table 1, page 73 of the report by M. Pianca et Al. "End groups in fluoropolymers", J. Fluorine Chem. 95 (1999), 71-84 (herein incorporated by reference); the found values express the concentrations of the residual —COF end groups as mmoles of end groups —COF/ Kg of polymer: in the fluoroelastomer spectrum no bands related to COF groups (1900-1836 cm$^{-1}$) are detectable, the method sensitivity limit being 0.05 mmoles/Kg.

More particularly the amount of —COF end groups in the polymer is determined by using the Nicolet® Nexus FT-IR equipment (256 scannings, resolution 2 cm$^{-1}$).

The fluoroelastomers according to the present invention preferably comprise also units deriving from bis-olefins of general formula:

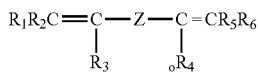
(I)

wherein:
$R_1, R_2, R_3, R_4, R_5, R_6$, equal to or different from each other, are H or $C_1$-$C_5$ alkyls;
Z is a $C_1$-$C_{18}$ linear or branched alkylene or cycloalkylene radical, optionally containing oxygen atoms, preferably at least partially fluorinated, or a (per)fluoropolyoxyalkylene radical, as described in patent EP 661,304 in the name of the Applicant.

The amount of bis-olefins is generally from 0.01 to 1.0% by moles, preferably from 0.03 to 0.5% by moles, still more preferably from 0.05 to 0.2 moles per 100 moles of the monomeric units, constituting the basic fluoroelastomer structure; the monomer total sum being 100%.

In formula (I), Z is preferably a $C_4$-$C_{12}$, more preferably $C_4$-$C_6$, perfluoroalkylene radical, while $R_1, R_2, R_3, R_4, R_5, R_6$ are preferably hydrogen; when Z is a (per)fluoropolyoxyalkylene radical, it can comprise units selected from the following:
—$CF_2CF_2O$—, —$CF_2CF(CF_3)O$—, —$CFX_1O$— wherein $X_1$=F, $CF_3$, —$CF_2CF_2CF_2O$—, —$CF_2$—$CH_2CH_2O$—, —$C_3F_6O$—.

Preferably Z has formula:

-$(Q)_p$-$CF_2O$—$(CF_2CF_2O)_m(CF_2O)_n$—$CF_2$-$(Q)_p$-   (II)

wherein: Q is a $C_1$-$C_{10}$ alkylene or oxyalkylene radical; p is 0 or 1; m and n are numbers such that the m/n ratio is between 0.2 and 5 and the molecular weight of said (per)fluoropolyoxyalkylene radical is in the range 500-10,000, preferably 700-2,000.

Preferably Q is selected from:
—$CH_2OCH_2$—; —$CH_2O(CH_2CH_2O)_sCH_2$—, s being=1-3.

The bis-olefins of formula (I) wherein Z is an alkylene or cycloalkylene radical can be prepared according to what described, for example, by I. L. Knunyants et al. in Izv. Akad. Nauk. SSSR, Ser. Khim., 1964(2), 384-6. The bis-olefins containing (per) fluoropolyoxyalkylene structures are described in U.S. Pat. No. 3,810,874.

More preferably the bis-olefin has formula:

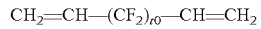

wherein t0 is an integer from 6 to 10.
The bis-olefin of formula:

(b).

is particularly preferred.

The fluoroelastomers of the invention are cured by peroxidic and/or ionic route. When the invention fluoroelastomers are cured by peroxidic route they contain preferably iodine and/or bromine, more preferably iodine in amounts generally between 0.001% and 5% by weight, preferably between 0.01% and 2.5% by weight with respect to the total polymer weight. The iodine atoms can be present in the chain and/or in end position.

To introduce iodine and/or bromine atoms along the chain, the copolymerization of the basic monomers of the fluoroelastomer is carried out with a suitable fluorinated comonomer containing iodine and/or bromine (cure-site monomers), see for example U.S. Pat. Nos. 4,745,165, 4,831,085, 4,214, 060, EP 683,149. Said fluorinated comonomer containing iodine can be selected for example from the following compounds:

(a) iodo(per)fluoroalkyl-perfluorovinylethers of formula:

(III)

wherein $R_f$ is a $C_1$-$C_{12}$ (per)fluoroalkylene, optionally containing chlorine and/or ether oxygen atoms;
for example: $ICF_2$—O—$CF$=$CF_2$, $ICF_2CF_2$—O—$CF$=$CF_2$, $ICF_2CF_2CF$—O—$CF$=$CF_2$, $CF_3CFICF_2$—O—$CF$=$CF_2$, and the like;

(b) iodo-(per)'fluoroolefins of formula:

(IV)

wherein $R'_f$ is a $C_1$-$C_{12}$ (per)fluoroalkylene, optionally containing chlorine atoms; for example: iodotrifluoroethylene, 1-iodo-2,2-difluoroethylene, iodo-3,3,4,4-tetrafluorobutene-1,4-iodo-perfluorobutene-1, and the like;

(c) iodo-(per)fluoroolefins of formula:

(V)

wherein: $R_o$ is H or —$CH_3$; $Z_o$ is a $C_1$-$C_1$-$C_{18}$ linear or branched (per)fluoroalkylene radical, optionally containing one or more oxygen atoms, or a (per) fluoropolyoxyalkylene radical as above defined.

Other cure-site iodinated comonomers are iodofluoroalkylvinylethers, see U.S. Pat. Nos. 4,745,165 and 4,564,662.

Alternatively, or in addition to the iodinated comonomer, the fluoroelastomer can contain iodine atoms in end position, deriving from a suitable iodinated chain transfer agent introduced in the reaction medium during the polymer preparation, as described in U.S. Pat. No. 4,501,869. Said transfer agents have formula $R^A_f(I)_x$, wherein $R^A_f$ is a $C_1$-$C_{12}$ (per)fluoroalkyl radical, optionally containing chlorine atoms, while x is 1 or 2. Said transfer agents can be selected, for example, from: $CF_2I_2$, $I(CF_2)_6I$, $I(CF_2)_4I$, $CF_2ClI$, $CF_3CFICF_2I$, and the like.

For the iodine introduced as chain end group by addition of iodinated chain transfer agents as above see for example U.S. Pat. Nos. 4,243,770 and 4,943,622.

It is also possible to use as chain transfer agents alkaline or alkaline-earth metal iodides, according to patent application EP 407,937.

In combination with the chain transfer agents containing iodine, other known chain transfer agents of the prior art, as ethyl acetate, diethylmalonate, etc., can be used.

The iodine amount in end position of the fluoroelastomer is generally between 0.001% and 3%, preferably between 0.01% and 1% by weight with respect to the fluoroelastomer weight. See U.S. Pat. Nos. 4,035,565 and 4,694,045.

Furthermore the curable fluoroelastomers can contain, alternatively or in combination with iodine, also bromine, in the chain and in end position. The bromine in the chain can be introduced according to known techniques; see for example U.S. Pat. Nos. 4,035,565, 4,745,165, EP 199,138; or as end bromine as described in U.S. Pat. No. 4,501,869.

Preferably the perfluoroelastomer contains iodine atoms in the chain and/or in end position.

Optionally the invention fluoroelastomers comprise in admixture a semicrystalline (per)fluoropolymer, in an amount in percent by weight referred to the total of the dry weight of the mixture fluoroelastomer+semicrystalline (per) fluoropolymer, from 0% to 70%, preferably from 0% to 50% by weight, still more preferably from 2% to 30% by weight.

With semicrystalline (per)fluoropolymer it is meant a (per) fluoropolymer showing, besides the glass transition temperature Tg, at least one crystalline melting temperature.

The semicrystalline (per)fluoropolymer is constituted of tetrafluoroethylene (TFE) homopolymers, or TFE copolymers with one or more monomers containing at least one unsaturation of ethylene type, in an amount from 0.01% to 10% by moles, preferably from 0.05% to 7% by moles.

Said comonomers having an ethylene unsaturation are both of hydrogenated and fluorinated type. Among those hydrogenated ethylene, propylene, acrylic monomers, for example methylmethacrylate, (meth)acrylic acid, butylacrylate, hydroxyethylhexylacrylate, styrene monomers, can be mentioned.

Among fluorinated comonomers it can be mentioned:
- $C_3$-$C_8$ perfluoroolefins, as hexafluoropropene (HFP), hexafluoroisobutene;
- $C_2$-$C_8$ hydrogenated fluoroolefins, as vinyl fluoride (VF), vinylidene fluoride (VDF), trifluoroethylene, perfluoroalkylethylene $CH_2$=$CH$—$R_f$, wherein $R_f$ is a $C_1$-$C_6$ perfluoroalkyl;
- $C_2$-$C_8$ chloro- and/or bromo- and/or iodo-fluoroolefins, as chlorotrifluoroethylene (CTFE);
- $CF_2$=$CFOR_f$ (per)fluoroalkylvinylethers (PAVE), wherein $R_f$ is a $C_1$-$C_6$ (per)fluoroalkyl, for example $CF_3$, $C_2F_5$, $C_3F_7$;
- $CF_2$=$CFOX$ (per)fluoro-oxyalkylvinylethers, wherein X is: a $C_1$-$C_{12}$ alkyl, or a $C_1$-$C_{12}$ oxyalkyl, or a $C_1$-$C_{12}$ (per)fluoro-oxyalkyl having one or more ether groups, for example perfluoro-2-propoxy-propyl; fluorodioxoles, preferably perfluorodioxoles.

PAVES, in particular perfluoromethyl-, ethyl-, propylvinylether and fluorodioxoles, preferably perfluorodioxoles, are preferred comonomers.

When the fluoroelastomers of the present invention contain semicrystalline (per)fluoropolymers, mixing is carried out by mixing in the desired ratios the fluoroelastomer latex with the semicrystalline perfluoropolymer latex and then co-coagulating the obtained mixture as described in U.S. Pat. Nos. 6,395,834 and 6,310,142.

Alternatively the semicrystalline (per)fluoropolymer can be polymerized and then the fluoroelastomer is polymerized on the (per)fluoropolymer particles. It is thus obtained a coreshell structure.

The Applicant has found that when the —COF end group amount in the fluoroelastomer, after polymerization, is substantially absent according to the above analysis method, it is obtained the best combination of mechanical and compression set properties in a wide temperature range, both at high and at low temperatures.

It is a further object of the present invention compositions comprising:
  fluoroelastomers of the present invention, having an amount of —COF end groups lower than 0.05 mmoles/Kg and Tg as above defined,
  and
  fluoroelastomers obtainable from polymers containing an amount of —COF end groups higher than 0.05 mmoles/Kg;
provided that the amount of fluoroelastomers of the present invention is at least 5-10% by weight, preferably 20-40% by weight, more preferably 50% by weight, with respect to the total weight of the fluoroelastomers in the composition.

These compositions can be obtained in various ways. For example, when monomers giving —COF end groups are used in polymerization, to obtain the improved properties according to the present invention it is carried out a part of polymerization of monomers in the absence of those giving —COF end groups, so as to obtain a polymer aliquot substantially —COF end group free which allows to obtain the combination of the above properties. For example the polymer obtained in the polymerization part carried out in the absence of monomers giving —COF end groups must be at least 5-10% by weight, preferably 20-40% by weight, more preferably 50% by weight, with respect to the final polymer weight. An alternative' process is that to mix the polymers of the present invention substantially —COF end group free with polymer's containing —COF in the above indicated ratios.

The fluoroelastomers containing —COF end groups in an amount higher than 0.05 mmoles/Kg comprise comonomers selected from the following:
  perfluorodioxoles, preferably having the following formula:

(2)

wherein
  Y=F, $ORf_1$, $Rf_1$ being a $C_1$-$C_5$ perfluoroalkyl, preferably $Rf_1$ is $CF_3$;
  $X_1$ and $X_2$, equal to or different from each other, are selected between F and $CF_3$, preferably F;
  $Z_1$ is selected among F, H, Cl, preferably F;
  perfluoroalkylvinylethers of formula $CF_2$=$CFORf$ wherein Rf is a $C_3$ perfluoroalkyl;
  $CF_2$=$CFOXa$ perfluorooxyalkylvinylethers, wherein Xa is $C_3$-$C_{12}$ perfluorooxyalkyl having one or more ether groups, for example perfluoro-2-propoxy-propyl;
  fluorovinylethers (MOVE) of general formula $CFX_{AI}$=$CX_{AI}OCF_2OR_{AI}$ (A-I) wherein $R_{AI}$ is a $C_2$-$C_6$ linear, branched or $C_5$-$C_6$ cyclic perfluoroalkyl group, or a $C_2$-$C_6$ linear or branched when possible perfluorooxyalkyl group containing from one to three oxygen atoms; when $R_{AI}$ is fluoroalkyl or fluorooxyalkyl as above defined it can contain from 1 to 2 atoms, equal or different, selected from the following: H, Cl, Br, I; $X_{AI}$=F, H; the compounds of general formula: $CFX_{AI}$=$CX_{AI}OCF_2OCF_2CF_2Y_{AI}$ (A-II) wherein $Y_{AI}$=F, $OCF_3$; $X_{AI}$ as above are preferred; in particular (MOVE 1) $CF_2$=$CFOCF_2OCF_2CF_3$ (A-III) and (MOVE 2) $CF_2$=$CFOCF_2OCF_2CF_2OCF_3$ (A-IV).

The curable fluoroelastomers of the invention preferably comprise the following monomers (percent by moles):
A) from 1% to 99%, preferably from 5% to 99%, of the monomer of formula:

(a)

B) one or more perfluorinated comonomers having at least one ethylene type unsaturation from 1% to 99%, preferably from 1 to 95%;
  said one or more comonomers comprising vinylidene fluoride (VDF) in an amount from 1% to 85% on the total of the monomer moles so that the polymer is fluoroelastomeric;

the sum of the monomer molar percentages being 100%; the —COF end group amount being as above.

When the polymer does not contain other monomers B) besides VDF, the monomer amount of formula (a) is not lower than about 15% by moles in order to obtain fluoroelastomeric poluymers.

Said fluoroelastomers preferably contain one bis-olefin.

More particularly the amount of —COF end groups in the polymer is determined by using the Nicolet® Nexus FT-IR apparatus (256 scannings, resolution 2 cm$^{-1}$).

Elastomeric polymers according to the present invention are polymers which, at the DSC (Differential Scanning calorimetry) analysis, do not show melting peaks, since the crystalline part is substantially absent.

When besides VDF other comonomers B) are present; they are selected from the following:

C$_2$-C$_8$ perfluoroolefins, for example TFE, hexafluoropropene, hexafluoroisobutene;

perfluoroalkylvinylethersof formula CF$_2$=CFORf wherein Rf is a C$_1$-C$_2$ perfluoroalkyl, preferably Rf=CF$_3$.

Tetrafluoroethylene (TFE) and/or perfluoromethylvinylether (MVE) are preferred comonomers B).

Preferred compositions (in % by moles) of the monomers constituting the basic structure of the copolymers of the present invention are the following, the sum of the monomer molar percentages being 100%; more preferably said compositions contain a bis-olefin:

monomer of formula (a): 15-40%, VDF: 60-85%; preferably monomer of formula (a): 15-40%, VDF: 60-85%, bis-olefin of formula (b): 0.01-1%;

monomer of formula (a): 15-40%, VDF: 60-85%, TFE: 5-40%; preferably monomer of formula (a): 15-40%, VDF: 60-85%; TFE: 5-40%, bis-olefin of formula (b): 0.01-1%;

monomer of formula (a): 5-40%, MVE: 5-30%, VDF: 50-85%; preferably monomer of formula (a): 5-40%, MVE: 5-30%, VDF: 50-85%, bis-olefin of formula (b): 0.01-1%;

monomer of formula (a): 5-40%, MVE: 5-30%, VDF: 50-85%, TFE: 5-40%; preferably monomer of formula (a): 5-40%, MVE: 5-30%, VDF: 50-85%, TFE: 5-40%, bis-olefin of formula (b): 0.01-1%;

monomer of formula (a): 40-99%, VDF: 1-60%; preferably monomer of formula (a): 40-99%, VDF: 1-60%, bis-olefin of formula (b): 0.01-1%;

monomer of formula (a): 40-99%, MVE: 0-30%, VDF: 1-60%; preferably monomer of formula (a): 40-99%, MVE: 0-30%, VDF: 60%, bis-olefin of formula (b): 0.01-1%;

monomer of formula (a): 40-99%, MVE: 0-30%, VDF: 1-60%, TFE: 5-40%; preferably monomer of formula (a): 40-99%, MVE: 0-30%, VDF: 1-60%, TFE: 5-40%, bis-olefin of formula (b): 0.01-1%.

As said, the fluoroelastomers of the invention show the improved combination of the above properties.

The fluoroelastomers of the present invention show a good elastic behaviour at low temperatures, as for example shown by the TR10 and TR70 values (ASTM D 1329).

The fluoroelastomers of the present invention compared with the fluoroelastomers of the prior art having a Tg lower than −35° C., the comparison being carried out with the same Tg, show improved mechanical and compression set properties and a higher resistance at high temperatures. In a comparison carried out with perfluoromethylvinylether based fluoroelastomers representing the most largely marketed fluoroelastomers for the applications at low temperatures, the fluoroelastomers of the present invention show a lower Tg and improved properties at low temperatures, as shown by the TR values.

The Applicant has found that the fluoroelastomers of the present invention are obtained with high polymerization kinetics, therefore it is possible to obtain homopolymers and copolymers having a high molecular weight. The fluoroelastomers of the present invention are obtainable with high yields and therefore the recovery of the unreacted monomers is useless, at the end of the polymerization. This allows to simplify the production plant, since the expensive recovery methods of unreacted monomers are not necessary.

The preparation of fluoroelastomers of the present invention is carried out by polymerization of the monomers in aqueous emulsion in the presence of an emulsion, dispersion or microemulsion of perfluoropolyoxyalkylenes, according to U.S. Pat. Nos. 4,789,717 and 4,864,006. Preferably the synthesis is carried out in the presence of a perfluoropolyoxyalkylene microemulsion.

According to well known methods of the prior art, radical initiators, for example alkaline or ammonium persulphates, perphosphates, perborates or percarbonates, optionally in combination with ferrous, cupreous or silver salts, or other easily oxidizable metals, are used. In the reaction medium also surfactants of various kind are optionally present, among which fluorinated surfactants of formula:

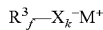

are particularly preferred, wherein $R^3_f$ is a $C_5$-$C_{16}$ (per)fluoroalkyl chain or (per)fluoropolycxyalkyl chain, $X_k^-$ is —COO$^-$ or —SO$_3^-$, M$^+$ is selected among: H$^+$, NH$_4^+$, or an alkaline metal ion. Among the most commonly used we remember: ammonium perfluorooctanoate, (per)fluoropolyoxyalkylenes ended with one or more carboxylic groups, etc. See U.S. Pat. Nos. 4,990,283 and 4,864,006.

The polymerization reaction is generally carried out at temperatures between 25° C. and 150° C., at a pressure between the atmospheric pressure up to 10 MPa.

In alternative or in combination with the chain transfer agents containing iodine and/or bromine, other chain transfer agents known in the prior art, as ethyl acetate, diethylmalonate, ethane, etc., can be used.

As said, the fluoroelastomers of the present invention are cured by peroxidic and/or ionic route.

In the peroxidic curing, preferably the fluoroelastomer contains in the chain and/or in end position to the macromolecule iodine and/or bromine atoms.

To the curing blend the following components are added:
peroxides capable to generate radicals by heating, for example: dialkylperoxides, in particular di-terbutyl-peroxide and 2,5-dimethyl-2,5-di(terbutylperoxy)hexane; dialkylarylperoxides as for example dicumyl peroxide; dibenzoyl peroxide; diterbutyl perbenzoate; di[1,3-dimethyl-3-(terbutylperoxy)butyl]-carbonate. Other peroxidic systems are described, for example, in European patent applications EP 136,596 and EP 410,351.
The peroxide amount is generally from 0.5% to 10% by weight with respect to the polymer, preferably 0.6%-4% by weight;
curing coagents, in amounts generally between 0.5 and 10%, preferably between 1 and 7%, by weight with respect to the polymer; among them, bis-olefins of formula (I); triallyl-cyanurate, triallyl-isocyanurate (TRIC), tris(diallylamine)-s-triazine; triallylphosphite; N,N-diallyl-acrylamide; N,N,N',N'-tetraallyl-malonamide; tri-vinyl-isocyanurate; and 4,6-tri-vinyl-methyl-trisiloxane, etc., are commonly used: TAIC and the bis-olefin of formula $$CH_2=CH-(CF_2)_6-CH=CH_2;$$

are particularly preferred;
optionally
a metal compound, in amounts between 1 and 15%, preferably from 2 to 10% by weight with respect to the polymer, selected from divalent metal oxides or hydroxides, as for example Mg, Zn, Ca or Pb, optionally combined with a weak acid salt, as stearates, benzoates, carbonates, oxalates or phosphites of Ba, Na, K, Pb, Ca;
other conventional additives, as mineral fillers, semicrystalline fluoropolymers in powder, pigments, antioxidants, stabilizers and the like.

When curing is carried out by ionic way, well known curing and accelerating agents in the prior art are added. The fluoroelastomer preferably in this case contains units deriving from HFP.

The accelerating agent amounts are in the range 0.05-5 phr, the curing agent in the range 0.5-15 phr, preferably 1-6 phr.

As curing agents, polyhydroxylated, aromatic or aliphatic compounds or their derivatives, can be used, as described for example in EP 335,705 and U.S. Pat. No. 4,233,427. Among them we remember in particular: di- tri- and tetra-hydroxy-benzenes, naphthalenes or anthracenes; bisphenols, wherein the two aromatic rings are connected each other by an aliphatic, cycloaliphatic or aromatic bivalent radical, or by one oxygen or sulphur atom, or also a carbonyl group. The aromatic rings can be substituted by one or more chlorine, fluorine, bromine atoms, or by carbonyls, alkyls, acyls. In particular the bisphenol AF is preferred.

As accelerating agents it can for example be used: quaternary ammonium or phosphonium salts (see for example EP 335,705 ed U.S. Pat. No. 3,876,654); amino-phosphonium salts (see for example U.S. Pat. No. 4,259,463); phosphoranes (see for example U.S. Pat. No. 3,752,787); imine compounds described in EP 182,299 and EP 120,462; etc. The quaternary phosphonium salts and the amino-phosphonium salts are preferred.

Instead of using the accelerating and the curing agent, it can also be used from 1 to 5 phr (from 2 to 4.5 preferred) of an adduct between an accelerating agent and a curing agent in a molar ratio from 1:2 to 1:5, preferably from 1:3 to 1:5, the accelerating agent being one of the onium-organic compounds having a positive charge, as above defined, the curing agent being selected from the above mentioned compounds, in particular di- or polyhydroxyl or di- or polythiol; the adduct being obtained by melting of the reaction product between accelerating agent and curing agent in the indicated molar ratios, or by melting of the mixture of the adduct 1:1 additioned with the curing agent in the indicated amounts. Optionally also an excess of the accelerating agent can be present with respect to that contained in the adduct, generally in amounts from 0.05 to 0.5 phr.

For the adduct preparation it is particularly preferred as cations: 1,1-diphenyl-1-benzyl-N-diethyl-phosphoranamine and tetrabutyl phosphonium; among anions, bisphenol compounds wherein the two aromatic rings are linked by a bivalent radical selected from perfluoroalkyl groups from 3 to 7 carbon atoms, and the OHs are in para positions, are particularly preferred.

The adduct preparation is described in the European patent application in the name of the Applicant EP 684,277 herein incorporated by reference.

The blend for the ionic curing contains furthermore:
i) one or more inorganic acid acceptors selected from those known in ionic curing of vinylidene fluoride copolymers, in amounts 1-40 parts per 100 parts of fluoroelastomeric copolymer;
ii) one or more basic compounds selected from those known in ionic curing of vinylidene fluoride copolymers, in amounts from 0.5 to 10 parts per 100 parts of fluoroelastomeric copolymer.

The basic compounds of point ii) are commonly selected in the group constituted by $Ca(OH)_2$, $Sr(OH)_2$, $Ba(OH)_2$, weak acid metal salts, such as for example carbonates, benzoates, oxalates and phosphites of Ca, Sr, Ba, Na and K and mixtures of the aforesaid hydroxides with the aforesaid metal salts; among the compounds of the type i) MgO can be mentioned.

The mentioned amounts of the components of the compounding are referred to 100 phr of the fluoroelastomer.

To the curing blend other conventional additives, such as thickeners, pigments, antioxidants, stabilizers and the like can then be added.

The semicrystalline (per)fluoropolymers, optional components of the present invention, are prepared according to the emulsion or microemulsion polymerization methods described above for the fluoroelastomers of the invention.

The monomer of formula (a) $CF_3OCF_2OCF=CF_2$ used in the polymers of the present invention can be prepared by a synthesis comprising the following steps:
I obtainment of the fluoroformate $CF_3OCOF$;
II reaction in liquid phase of the fluoroformate $CF_3OCOF$ with elemental fluorine and olefinic compounds having formula:

$$CAF=CA'F \quad (IV)$$

for obtaining the fluorohalogenether of formula:

$$CF_3OCF_2OCFACF_2A' \quad (V)$$

wherein A and A', equal to or different the one from the other, are H, Cl or Br, with the proviso that both are not H; the fluorination reaction temperature can range from −120° C. to −20° C., preferably from −100° C. to −40° C.; optionally one operates in the presence of a perhalogenated solvent, liquid and inert under the reaction conditions; the fluorine can optionally be diluted with an inert gas, e.g. nitrogen or helium;
III removal of the substituents A and A' from the fluorohalogenether (V) by a dehalogenation when A and A' are halogen, or a dehydrohalogenation when one of A or A' is hydrogen and the other is halogen;
the fluoroformate $CF_3OCOF$ of step I can be prepared with high conversion and selectivity by thermal reaction, in gaseous phase, of $CF_3OF$ (fluoroxyperfluoromethane) with CO in a reactor maintained at temperatures between 80° C. and 250° C., preferably between 120° C. and 230° C., still more preferably between 150° C. and 200° C.

The dehaldgenation or dehydrohalogenation reactions used are well known in the prior art.

The molar ratio $CF_3OF/CO$ is between 0.1 and 10, preferably between 0.2 and 5, more preferably between 0.5 and 2.

The perhalogenated solvent optionally used in step II, is preferably an organic compound containing fluorine and/or chlorine, optionally one or more oxygen atoms in the chain and/or aminic groups as end group.

When the perhalogenated solvent is perfluorinated, it can for example be selected among perfluorocarbons, perfluoroethers, perfluoropolyethers, perfluoroamines, or respective Mixtures.

The reaction mixture containing $CF_3OCOF$ of step I can be directly fed, without separation of the mixture components, into the other reactor for the reaction of step II. The process for obtaining the monomer of step I starting from $CF_3OF$ resulted particularly simple and effective. As said, the $CF_3OF$ conversion and the selectivity to $CF_3OCOF$ are high (see the Examples).

In step I, by increasing the reaction temperature in the range 80°-250° C., the conversion increases and, at the same time, a high selectivity is substantially maintained.

Alternatively, the $CF_3OCOF$ of step I can be prepared by photochemical route, in liquid phase, by feeding the two reactants as indicated above into a reactor equipped with a mercury high pressure UV lamp, contained in a cooled quartz sheath, immersed in the reaction mixture at temperatures between 0° C. and 100° C., preferably between 20° C. and 50° C.

It has been found that the formation reaction of the fluoroformate by photochemical route has a high selectivity, and that higher yields are obtained compared with the same reaction carried out in gaseous phase.

The reaction by photochemical route is carried out in the presence of an inert perfluorinated solvent, liquid under the reaction conditions.

Preferably the perfluorinated solvent is selected from perfluorocarbons, perfluoropolyethers, perfluorinated tertiary amines, fluorochlorocarbons, or mixtures thereof.

When the $CF_3OF$ conversion is not quantitative, the gaseous flow leaving the reactor contains a mixture formed of the reaction product together with unconverted CO and $CF_3OF$ The latter can be removed by passing the gaseous flow into a cold trap containing a fluorinated olefin, for example $CFCl=CFCl$; then, by fractional distillation, $CF_3OCOF$ is separated.

Alternatively the gaseous reaction mixture containing the reaction products formed in step I is cooled to condensate the fluoroformate, separating $CF_3OF$ and CO which can be recycled into the reactor.

Preferably step I is carried out by reacting the fluorooxyperfluoromethane and carbon monoxide at temperatures from 80° C. to 250° C.

Preferably the reactor used in step I is made of glass, inert perfluorinated plastics, as for example PTFE, PFA, metal alloys, for example AISI 316, preferably coated with glass or perlfluorinated plastics. More preferably, as materials glass or fluorinated plastics are used.

The fluoroelastomers of the present invention, as said, show an improved combination at high temperatures of mechanical properties, in particular modulus, stress at break and elongation at break, of elastomeric properties as shown by the compression set, and of thermal resistance; and contemporaneously they show an improved combination of the above mentioned properties even at low temperatures.

With the fluoroelastomers of the present invention manufactured articles for temperatures lower than –35° C. up to 250° C., having improved mechanical and elastomeric properties, can be obtained.

The following Examples illustrate with non limitative purpose the present invention.

EXAMPLES

Analytical Methods
Determination of the Polymer Tg
The Tg has been determined by DSC analysis according to the ASTM D 3418 method. The Tg values reported in the Examples are the mid-point Tg.

Determination of the Intrinsic Viscosity
The intrinsic viscosity has been determined in perfluoroheptane at the temperature of 30° C.
Determination of the —COF Polar End Groups
At the end of the polymerization, the polymer is isolated by coagulation by freezing at –20° C. and subsequent defrosting at room temperature until obtaining a slurry wherein the polymer deposits on the bottom; it is washed twice with demineralized water and it is dried in a stove at 90° C. up to a constant weight (about 12 hours); the —COF end groups are determined by FT-IR spectroscopy, by using the Nicolet® Nexus FT-IR equipment (256 scannings, resolution 2 $cm^{-1}$), wherein on a polymer film having a thickness from 50 to 300 micron a scanning between 4000 $cm^{-1}$ and 400 $cm^{-1}$ is initially carried out, the film being then kept for 12 hours in an environment saturated with ammonia vapours, and recording at the end the IR spectrum under the same conditions of the initial IR spectrum; elaborating the two spectra by subtracting to the signals of the spectrum related to the untreated specimen (initial spectrum) the corresponding signals of the specimen spectrum after exposure to ammonia vapours, drawing the "difference" spectrum, normalized by the following equation:

$$\frac{\text{"Difference spectrum"}}{[\text{film weight (g)/film area (cm}^2)]};$$

the optical densities related to the —COF end groups, reacted with the ammonia vapours, which with this reactant give detectable peaks, are measured; the optical densities are converted into mmoles/kg of polymer by using the molar extinction coefficient of the —COF group at 1884 $cm^{-1}$, equal to 215 litres/(moles×cm), as reported Table 1, page 73 of the report by M. Pianca et Al. "End groups in fluoropolymers", J. Fluorine Chem. 95 (1999), 71-84 (herein incorporated by reference); the found values express the concentrations of the residual —COF end groups as mmoles of end groups —COF/Kg of polymer: in the fluoroelastomer spectrum no bands related to COF groups (1900-1830 $cm^{-1}$) are detectable, the method sensitivity limit being 0.05 mmoles/Kg.
Mooney Viscosity Determination
The Mooney viscosity (1+10' at 121° C.) is determined according to the ASTM D 1646 method.
Compression Set Determination
The Compression Set is determined according to the ASTM D 395 method.
TR Determination
The TR Test is determined according to the ASTM D 1329 method.

Example A

Preparation of $CF_3OCOF$ by Thermal Reaction at 170° C. in Glass Reactor

A tubular glass reactor is used, having an inner diameter of 55.6 mm and length of 510 mm, filled with 6×6 glass Raschig rings (free internal volume 842 ml), maintained thermostated by electric resistances.

A gaseous flow of $CF_3OF$ (1.5 litres/hour), synthesized as described in U.S. Pat. No. 4,400,872 and, contemporaneously, a CO flow (1.5 litres/hour), are fed for 5 hours into the reactor, maintained at the temperature of 170° C. The flow coming out from the reactor is continuously analyzed by online gaschromatographic analysis.

The flow coming out from the reactor is condensed, except CO, in a trap maintained at −110° C. containing 15 g of CFCl=CFCl (A 1112), so that the residual $CF_3OF$ reacts with the olefin to give $CF_3OCFClCF_2Cl$.

After fractional distillation of the resulting mixture, 33.9 g of $CF_3OCOF$ pure at 99.8% (molar yield on the fed $CF_3OF$ 76.5%); 12.3 g of $CF_3OCFClCF_2Cl$; 3.4 g of $COF_2$ are obtained.

The conversion is 84.5% and the selectivity 90%, calculated on the fed $CF_3OF$

Example B

Preparation of $CF_2OCOF$ by Thermal Reaction at 170° C. in PTFE Reactor

A PTFE tubular thermostated reactor is used, having an internal diameter of 4 mm and length of 13.2 m.

A gaseous flow of $CF_3OF$ (1.5 litres/hour) and, contemporaneously, a flow of CO (2.0 litres/hour) are fed into the reactor, maintained at the temperature of 170° C.

The flow coming out from the reactor, analyzed by gaschromatography, has the following molar composition: 7.3% $CF_3OF$, 54.2% $CF_3OCOF$, 9.1% $COF_2$ and 29.4% CO.

Example C

Preparation of $CF_3OCOF$ by Thermal Reaction at 120° C. in PTFE Reactor

A gaseous flow of $CF_3OF$ (1.5 litres/hour) and, contemporaneously, a flow of CO (2.0 litres/hour) are fed for 6 hours into the same reactor used in the Example B, maintained at the temperature of 120° C. The flow coming out from the reactor is analyzed by gaschromatography and has the following molar composition, leaving out CO in excess: 86.7% $CF_3OF$, 13.3% $CF_3OCOF$.

The flow coming out from the reactor is condensed, except CO, in a trap maintained at −110° C. containing 50 g of A 1112, so that the residual $CF_3OF$ reacts with the olefin.

After fractional distillation of the resulting mixture, 6.8 g of $CF_3OCOF$ having a 99% purity are obtained.

The selectivity is 98%, calculated on the converted $CF_3OF$
The conversion is 13.0%.

Example D

Preparation of $CF_3OCOF$ by Thermal Reaction at 170° C. in AISI 316 Reactor

An AISI 316 tubular thermostated reactor is used, having an internal diameter of 4 mm and length of 11.3 m.

A gaseous flow of $CF_3OF$ (1.5 litres/hour) and, contemporaneously, a flow of CO (1.5 litres/hour) are fed for 6 hours into the reactor, maintained at the temperature of 170° C. The gaseous flow coming out from the reactor is condensed in a trap maintained at −110° C. containing 30 g of A 1112.

After fractional distillation of the trap content, 31.2 g of $CF_3OCOF$ pure at 99%, 31.8 g of fluorohalogenether and 3.7 g of $COF_2$ are obtained. The conversion is 66.6% and the selectivity is 86.5%.

Example E

Preparation of $CF_3OCOF$ by Photochemical Reaction 500 g of a perfluoropolyether Galden®LS-165 are fed into a 300 ml cylindrical glass reactor, equipped with stirrer and UV lamp Hanau TQ 150, with 150 W power and optical route 1 cm. Then 2.0 litres/hour of $CF_3OF$ diluted with 3.0 litres/hour of He, and 2.0 litres/hour of CO are fed contemporaneously for 5 hours.

The gases coming out from the reactor are condensed in a trap maintained at −110° C. containing 30 g of A 1112. After fractional, distillation of the condensed mixture, 22.9 g of $CF_3OCOF$ pure at 99%, 41.8 g of fluorohalogenether $CF_3OCFClCF_2$—Cl, 5.8 g of $COF_2$, 5.4 g of trifluoromethyl carbonate are obtained.

The $CF_3OF$ conversion is 60.5%. The selectivity is 63.6%.

Example F

Obtainment of the Monomer of Formula (a) by Reaction of $CF_3O$—COF with Elemental Fluorine and a Fluoroolefin of Formula CFCl=CFCl and Subsequent Fluorohalogenether Dehalogenation 20 g of CFCl=CFCl (A 1112), 30 g of $CF_3OCOF$ obtained as in the Example A are transferred in a 50 ml glass reactor. The solution formed is maintained at −100° C. and fluorine diluted with nitrogen is bubbled at a flow of 1 litre/hour.

The mass balance at the end of the reaction is 92%, the $^{19}$F-NMR analysis on the reaction raw product (52 g) shows that the fluoroformate conversion is 54% and the selectivity to give the fluorohalogenether $CF_3OCF_2OCFClCF_2Cl$ is 93%. The unreacted fluoroformate is removed from the reaction raw product by adding water, under stirring. It is let reach 25° C., the organic phase is recovered and dried over $MgSO_4$. The mixture is filtered and the obtained residue is distilled and the fraction boiling at 74° C. of 31.8 g corresponding to the fluorohalogenether having 99% purity is recovered.

The fluorohalogenether dehalogenation is carried out by using an 1 litre flask equipped with mechanical stirrer, thermometer, funnel dropping, distillation column and trap at −78° C. 450 ml of dimethylformamide (DMF), 62 g of zinc in powder and 8.3 g of $ZnCl_2$ are fed into the flask. The temperature in the suspension is brought to 80° C. and 150 g of the fluorohalogenether isolated in the previous reaction are added. When the addition is over, the mixture is let react for one hour. At the end the temperature is gradually increased up to 120° C. and it is let react still for one hour. Lastly it is disconnected and 106 g of the monomer of formula (a) $CF_3OCF_2OCF=CF_2$ having 99% purity (boiling point 23° C.) are recovered therefrom.

Example 1

Preparation of the Microemulsion

The microemulsion is obtained by mixing the following ingredients in the amounts indicated hereinafter to prepare one litre of microemulsion:

220.7 ml of a perfluoropolyoxyalkylene having acid end group with average molecular weight 600, of formula:

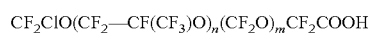
$CF_2ClO(CF_2—CF(CF_3)O)_n(CF_2O)_mCF_2COOH$ wherein n/m=10;

220.7 ml of an aqueous solution of $NH_3$ at 30% by volume;

427.6 ml of demineralized water;

131 ml of Galden® D02, having average molecular weight 450, of formula:

$CF_3O(CF_2—CF(CF_3)O)_n(CF_2O)_mCF_3$ wherein n/m=20.

Example 2

Copolymer Monomer of Formula (a)/VDF 75/25 (% by Moles Ratio)

20 ml of demineralized water, 1 ml of microemulsion prepared in the Example 1 are introduced in sequence into a 42 ml steel autoclave, equipped with magnetic stirring, after vacuum has been made by oil pump. 9 g of the monomer of formula (a) are added and the autoclave is heated to 80° C. VDF is introduced in the reactor until bringing the pressure to 1.5 MPa. Then 4 mg of ammonium persulphate are introduced. The reaction pressure is maintained constant by addition of VDF at every pressure decrease equal to 0.01 MPa.

The reaction ends after 6 h. The obtained latex is degassed. The latex is coagulated by freezing and subsequent defrosting. In this way the polymer is separated from the aqueous phase; it is washed twice with demineralized water and dried in a stove at 100° C. for 8 h. About 8.0 g of polymer equal to 90% of the fed monomer of formula (a) are obtained. The polymer Tg is −54.3° C. The intrinsic viscosity measured at 30° C. in perfluoroheptane (Galden® D80) is equal to 40.8 cc/g.

By NMR analysis the polymer composition is determined; it contains 75% by moles of the monomer of formula (a):

By IR analysis it is found that the —COF end groups in the polymer are lower than the method sensitivity limit.

Example 3 (Comparative)

Copolymerization of MOVE 1 with VDF Under the Conditions of Example 2

One proceeds as in the Example 2, but by introducing 9 g of MOVE 1 at the place of the monomer of formula (a). The polymerization starts after 5 minutes from the initiator introduction and ends after 6 hours.

The obtained polymer amount is equal to 3 g.

By NMR analysis the polymer composition is determined; it contains 20% by moles of MOVE 1 equal to 52% of fed MOVE 1 monomer.

By IR analysis it is found that the —COF end groups in the polymer are detectable with the above method and therefore they are >0.05 mmoles/Kg.

Comments to Example 2 of the Invention and Example 3 Comparative

The remarkable reactivity of monomer (a) over MOVE 1 can be drawn by comparing the % of vinilethereal monomers in the copolymers of example 2 and comparative example 3. These examples show that under similar polymerization conditions, by using as vinylether monomer (a) instead of MOVE 1, in the polymer of example 2 it is incorporated a quantity of monomer (a) of 75% by moles, whereas in comparative example 3 that uses MOVE 1, in the polymer it is found an amount of 20% by moles of MOVE 1. Further, the copolymer of example 2 is free of —COF end groups, while the same end groups are present in the polymer of comparative example 3, even if it contains a remarkable lower quantity of the vinylether.

Example 2 highlights the surprising and unexpected behavior of monomer (a): the Tg of the copolymer of this example is −54.3° C. It must be remarked that it is much lower than the Tg of the homopolymers of monomer (a), i.e. −39.4, (see example 9), and also of the homopolymer of VDF, i.e. −47° C.

Example 4

Copolymer Monomer (a)/VDF 21/79 (% by Moles Ratio)

In a 5 lt autoclave, equipped with stirrer working at 630 rpm, there were introduced, after evacuation, 3.0 it of demineralized water and 30 ml of microemulsion of perfluoropolyoxyalkylenes previously obtained as in example 1. The autoclave was then heated up to 60° C. and maintained at said temperature for the whole reaction. The following mixture of monomers was then fed: vinylidene fluoride (VDF) 75% by moles, monomer (a) 25% by moles, so as to bring the pressure up to 1.1 Mpa. In the autoclave there were then introduced: 3.75 gr of ammonium persulphate (APS) as initiator; 5.48 gr of 1,4-diiodo perfluorobutane ($C_4F_8I_2$) as polymer chain transfer agent; 2.26 gr of a bis-olefin of formula $CH_2$=CH—$(CF_2)_6$—CH=$CH_2$; the addition of the bis-olefin was carried out in 20 aliquots, each of 0.113 gr starting from the beginning of the polymerization and for every 5% increase in the monomer conversion. The pressure of 1.1 Mpa was maintained constant for the whole polymerization by feeding a mixture formed by: vinylidene fluoride (VDF) 75% by moles, monomer (a) 25% by moles. After 189 minutes of reaction, corresponding to 100% of the monomer conversion, the autoclave was cooled and the latex discharged. The so obtained latex is coagulated with a solution of aluminum sulphate (6 gr of $Al_2(SO_4)_3$ for each litre of latex) and dried at 90° C. in an air circulating over for 16 hours. 580 gr of polymer were obtained.

By $^{19}$F-NMR analysis of the polymer dissolved in hot acetone it is found that the molar percentage of monomer (a) in the polymer is 21%, and of VDF is 79%. The $T_g$, determined by DSC is −47.9° C.

The Mooney viscosity (ML(1+10' at 121° C.)) determined according to the ASTM D 1646 method is 20 MU. The mechanical properties are shown in Table 1.

Example 5

Terpolymer Monomer (a)/VDF/TFE 21/53/26 (% by Moles Ratio)

In a 5 lt autoclave, equipped with stirrer working at 630 rpm, there were introduced, after evacuation, 3.0 lt of demineralized water and 30 ml of microemulsion of perfluoro polyoxyalkylenes previously obtained as in example 1. The autoclave was then heated up to 70° C. and maintained at said temperature for the whole reaction. The following mixture of monomers was then fed: vinylidene fluoride (VDF) 53% by moles monomer (a) 21% by moles, tetrafluoroethylene (TFE) 26% by moles, so as to bring the pressure up to 1.1 Mpa. In the autoclave there were then introduced: 0.3 gr of ammonium persulphate (APS) as initiator; 4.29 gr of 1,4-diiodo perfluorobutane ($C_4F_8I_2$) as polymer chain transfer agent; 2.26 gr of a bis-olefin of formula $CH_2$=CH—$(CF_2)_6$—CH=$CH_2$; the addition of the bis-olefin was carried out in 20 aliquots, each of 0.113 gr starting from the beginning of the polymerization and for every 5% increase in the monomer conversion. The pressure of 1.1 MPa was maintained constant for the whole polymerization by feeding a mixture formed by: vinylidene fluoride (VDF), 49% by moles; monomer (a) 25% by moles, tetrafluoroethylene (TFE) 26% by moles. After 132 minutes of reaction, corresponding to 100% of the monomer conversion, the autoclave was cooled and the latex discharged. The latex was coagulated as in ex. 4. 583 gr of polymer were obtained.

By $^{19}$F-NMR analysis of the polymer dissolved in hot acetone it is found that the molar percentage of monomer (a) in the polymer is 21%, of VDF is 53% and of TFE is 26%. The $T_g$, determined by DSC is −43.6° C. The Mooney viscosity (ML(1+10' at 121° C.)) determined according to the ASTM D 1646 method is 22 MU. By IR analysis it is found that the —COF end groups in the polymer are lower than the method sensitivity limit. The mechanical properties are shown in Table 1.

Example 6

Tetrapolymer of Monomer (a)/VDF/TFE/HFP 15/62/16/7 (% by Moles Ratio)

In a 5 lt autoclave, equipped with stirrer working at 630 rpm, there were introduced, after evacuation, 3.0 lt of demineralized water and 30 ml of microemulsion of perfluoro polyoxyalkylenes previously obtained as in example 1. The autoclave was then heated up to 70° C. and maintained at said temperature for the whole reaction. The following mixture of monomers was then fed: vinylidene fluoride (VDF) 53% by moles, monomer (a) 10% by moles, tetrafluoroethylene (TFE) 20% by moles, hexafluoropropene (HFP) 17% by moles, so as to bring the pressure up to 1.1 MPa. In the autoclave there were then introduced: 0.45 gr of ammonium persulphate (APS) as initiator; 5.05 gr of 1,4-diiodoperfluorobutane ($C_4F_8I_2$) as polymer chain transfer agent; 2.26 gr of a bis-olefin of formula $CH_2=CH-(CF_2)_6-CH=CH_2$; the addition of the bis-olefin was carried out in 20 aliquots, each of 0.113 gr starting from the beginning of the polymerization and for every 5% increase in the monomer conversion. The pressure of 1.1 MPa was maintained constant for the whole polymerization by feeding a mixture formed by: vinylidene fluoride (VDF) 64% by moles, monomer (a) 13% by moles, tetrafluoroethylene (TFE) 13% by moles, hexafluoro propene (HFP) 10% by moles. After 118 minutes of reaction, corresponding to 100% of the monomer conversion, the autoclave was cooled and the latex discharged. The latex was coagulated as in ex. 4. 583 gr of polymer was obtained. 568 gr of polymer were obtained.

By $^{19}$F-NMR analysis of the polymer dissolved in hot acetone it is found that the molar percentage of monomer (a) in the polymer is 14.6%, of VDF is 62.4%, of TFE is 15.6% and of HFP is 7.4%. The $T_g$, determined by DSC, is −37.2° C. The Mooney viscosity (ML(1+10' at 121° C.)) determined according to the ASTM D 1646 method is 9 MU. By IR analysis it is found that the —COF end groups in the polymer are lower than the method sensitivity limit (0.05 mmoles/Kg). The mechanical properties are shown in Table 1.

Example 7

Tetrapolymer Monomer (a)/VDF/TFE/MVE 15/57/22/6 (% by Moles Ratio)

In a 5 lt autoclave, equipped with stirrer working at 630 rpm, there were introduced, after evacuation, 3.5 lt of demineralized water and 35 ml of microemulsion of perfluoropolyoxyalkylenes previously obtained as in example 1. The autoclave was then heated up to 70° C. and maintained at said temperature for the whole reaction. The following mixture of monomers was then fed: vinylidene fluoride (VDF) 44% by moles, monomer (a) 20% by moles, tetrafluoroethylene (TFE) 21% by moles, methylvinylether (MVE) 13% by moles, so as to bring the pressure up to 1.6 Mpa. In the autoclave there were then introduced: 0.35 gr of ammonium persulphate (APS) as initiator; 5.05 gr of 1,4-diiodoperfluorobutane ($C_4F_8I_2$) as polymer chain transfer agent; 2.26 gr of a bis-olefin of formula $CH_2=CH-(CF_2)_6-CH=CH_2$; the addition of the bis-olefin was carried out in 20 aliquots, each of 0.113 gr starting from the beginning of the polymerization and for every 5% increase in the monomer conversion. The pressure of 1.6 MPa was maintained constant for the whole polymerization by feeding a mixture formed by: vinylidene fluoride (VDF) 51% by moles, monomer (a) 15% by moles, tetrafluoroethylene (TFE) 26% by moles, methylvinylether (MVE) 8% by moles. After 90 minutes of reaction, corresponding to 100% of the monomer conversion, the autoclave was cooled and the latex discharged. The latex was coagulated as in ex. 4. 603 gr of polymer were obtained.

By $^{19}$F-NMR analysis of the polymer dissolved in hot acetone, it is found that the molar percentage of monomer (a) is 14.6%, of TFE is 21.7%, of VDF is 57.5%, of MVE is 6.2%. The $T_g$, determined by DSC is −38.4° C. The Mooney viscosity (ML(1+10' at 121° C.)) determined according to the ASTM D 1646 method is 20 MU. The mechanical properties are shown in Table 1.

Example 8

Tetrapolymer Monomer (a)/VDF/TFE/MVE 16/62/15/7 (% by Moles Ratio)

In a 5 lt autoclave, equipped with stirrer working at 630 rpm, there were introduced, after evacuation, 3.5 lt of demineralized water and 35 ml of microemulsion of perfluoropolyoxyalkylenes previously obtained as in example 1. The autoclave was then heated up to 70° C. and maintained at said temperature for the whole reaction. The following mixture of monomers was then fed: vinylidene fluoride (VDF) 44% by moles, monomer (a) 20% by moles, tetrafluoroethylene (TFE) 23% by moles, methylvinylether (MVE) 13% by moles, so as to bring the pressure up to 1.6 Mpa. In the autoclave there were then introduced: 0.35 gr of ammonium persulphate (APS) as initiator; 5.05 gr of 1,4-diiodo perfluorobutane ($C_4F_8I_2$) as polymer chain transfer agent; 2.26 gr of a bis-olefin of formula $CH_2=CH-(CF_2)_6-CH=CH_2$; the addition of the bis-olefin was carried out in 20 aliquots, each of 0.113 gr starting from the beginning of the polymerization and for every 5% increase in the monomer conversion. The pressure of 1.6 MPa was maintained constant for the whole polymerization by feeding a mixture formed by: vinylidene fluoride (VDF), 61% by moles, monomer (a) 16% by moles, tetrafluoroethylene (TFE) 15% by moles, methylvinylether (MVE) 8% by moles. After 97 minutes of reaction, corresponding to 100% of the monomer conversion, the autoclave was cooled and the latex discharged. The latex was coagulated as in ex. 4. 598 gr of polymer were obtained.

By $^{19}$F-NMR analysis of the polymer dissolved in hot acetone it is found that the molar percentage of monomer (a) is 15.8%, of TFE is 15.4%, of VDF is 61.6% and of MVE is 7.2%. The $T_g$, determined by DSC is −40.9° C. The Mooney viscosity (ML(1+10' at 121° C.)) determined according to the ASTM D 1646 method is 24 MU. The mechanical properties are shown in Table 1.

Example 9

Homopolymer of the Monomer of Formula (a)

0.03 l of demineralized water, 1.5 ml of the microemulsion of the Example 1, and 12 g of the monomer of formula (a) are introduced in sequence into a 0.1 l (litres) glass autoclave, equipped with magnetic stirring, after vacuum has been made by oil pump. The autoclave is heated to 42° C. Then 0.1 g of ammonium persulphate are introduced. The reactor is maintained at 42° C. for 170 h and then cooled. The obtained latex is degassed. The latex is coagulated by freezing and subsequent defrosting. In this way the polymer is separated from the aqueous phase; it is washed twice with demineralized water and dried in a stove at 100° C. for 8 h.

About 11 g of polymer equal to a conversion of 92% of the fed monomer of formula (a) are obtained. The polymer Tg is −39.4° C. The intrinsic viscosity measured at 30° C. in perfluoroheptane (Galden® D80) is equal to 30.5 cc/g. By IR analysis it is found that the —COF end groups in the polymer are lower than the method sensitivity limit.

Conversions of about 69% of the monomer of formula (a) are obtained with lower polymerization times.

Comments to Examples 4-9

These examples show that monomer (a) can be copolymerized with various comonomers allowing to prepare polymers wherein the relevant quantities of the comonomers can be varied within a wide range of polymer compositions. This allows to reach the best combination of polymer properties.

As an example, it is possible to lower the hydrogen content in the polymer in order to increase its chemical resistance, while maintaining good low temperature properties. See examples 6 and 7, wherein it is described the preparation of polymers having the same TR 10 and showing a different hydrogen content.

Further, it has unexpectedly and surprisingly found that the Tg values of the copolymers are lower than those of the values of the corresponding homopolymers of monomer (a) and of the other(s) comonomer(s) of the polymer.

TABLE 1

| | | EXAMPLES | | | | |
|---|---|---|---|---|---|---|
| | | 4 | 5 | 6 | 7 | 8 |
| Formulation: | | | | | | |
| Luperco 101 XL 45 | phr | 2 | 2 | 2 | 2 | 2 |
| Drimix TAIC 75% | " | 5 | 5 | 5 | 5 | 5 |
| ZnO | " | 5 | 5 | 5 | 5 | 5 |
| Black MT N990 | " | 30 | 30 | 30 | 30 | 30 |
| Mooney polymer ML$_{121}$* (1 + 10) | | 20 | 22 | 9 | 20 | 24 |
| MDR 160° C., 12' (ASTM D6204-97): | | | | | | |
| ML | Lbf · in. | 0.5 | 0.46 | 0.19 | 0.57 | 0.7 |
| MH | " | 29.5 | 29.0 | 26.7 | 32.6 | 28.7 |
| ts2 | " | 68 | 48 | 65 | 50 | 57 |
| t'50 | " | 116 | 104 | 122 | 112 | 119 |
| t'90 | " | 233 | 196 | 224 | 201 | 220 |
| Mechanical properties after post-cure at 230° C. for 1 + 4 h (ASTM D412-83) | | | | | | |
| M100 | Mpa | 7.4 | 8.2 | 6.1 | 10.2 | 7.9 |
| Stress at break | " | 15 | 12.8 | 15.9 | 14.2 | 13.4 |
| Elong. at break | % | 160 | 134 | 191 | 125 | 142 |
| Hardness Shore A | | 71 | 72 | 71 | 71 | 69 |
| Compression set 200° C. for 70 h | | | | | | |
| O-ring (ASTM D 395) | % | 24 | 22 | 24 | 18 | 21 |
| TR 10 (ASTM D1329) | ° C. | −45 | −42 | −36 | −37 | −40 |
| TR 70 (ASTM D1329) | ° C. | −37 | −33 | −28 | −30 | −33 |

The invention claimed is:

1. A process to obtain the monomer $CF_3OCF_2OCF=CF_2$ comprising the following steps:
   I obtainment of the fluoroformate $CF_3OCOF$;
   II reaction of the fluoroformate $CF_3OCOF$ with elemental fluorine and olefinic compounds having formula:

$$CAF=CA'F \quad (IV)$$

for obtaining the fluorohalogenether of formula $$CF_3OCF_2OCFACF_2A' \quad (V)$$

wherein A and A', equal to or different the one from the other, are H, Cl or Br, with the proviso that both are not H;
   the temperature being between −120° C. and −20° C.;
   III removal of the substituents A and A' from the fluorohalogenether (V).

2. A process according to claim 1, wherein in step I the fluoroformate $CF_3OCOF$ is prepared by reaction of $CF_3OF$ with CO at temperatures between 80° C. and 250° C.

3. A process according to claim 2, wherein in step I the temperature ranges from 120° C. to 230° C.

4. A process according to claim 2, wherein in step I the temperature ranges from 150° C. to 200° C.

5. A process according to claim 2, wherein in step I the molar ratio $CF_3OF/CO$ is between 0.1 and 10.

6. A process according to claim 2, wherein in step I the molar ratio $CF_3OF/CO$ is between 0.2 and 5.

7. A process according to claim 2, wherein in step I the molar ratio $CF_3OF/CO$ is between 0.5 and 2.

8. A process according to claim 1, wherein in step II it is operated in the presence of a perhalogenated solvent, liquid and inert under the reaction conditions.

9. A process according to claim 8, wherein the perhalogenated solvent is an organic compound containing fluorine and/or chlorine.

10. A process according to claim 8, wherein the perhalogenated solvent contains one or more oxygen atoms in the chain and/or aminic groups as end group.

11. A process according to claim 8, wherein the perhalogenated solvent is perfluorinated.

12. A process according to claim 11, wherein the perfluorinated solvent is selected from perfluorocarbons perfluoroethers, perfluoropolyethers or perfluoroamines, and mixtures thereof.

13. A process according to claim 1, wherein in step II fluorine is diluted with an inert gas.

14. A process according to claim 13, wherein the inert gas is selected from nitrogen or helium.

15. A process according to claim 1, wherein in step I the reaction mixture containing $CF_3OCOF$ is directly fed, without separation of the mixture components, into the reactor of step II.

16. A process according to claim 1, wherein the reactor used in step I is made of glass, inert perfluorinated plastics, or of metal alloys coated inside with glass or with perfluorinated plastics.

17. A process according to claim 16, wherein the perfluorinated plastics are selected from PTFE, PFA.

* * * * *